United States Patent
House

(10) Patent No.: US 9,606,148 B2
(45) Date of Patent: Mar. 28, 2017

(54) CHEMICAL/BIOLOGICAL SENSORS EMPLOYING FUNCTIONALIZED NANOSWITCH ARRAY

(71) Applicant: Battelle Memorial Institute, Columbus, OH (US)

(72) Inventor: Larry J. House, Columbus, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 859 days.

(21) Appl. No.: 13/850,366

(22) Filed: Mar. 26, 2013

(65) Prior Publication Data

US 2013/0249574 A1   Sep. 26, 2013

Related U.S. Application Data

(60) Provisional application No. 61/615,519, filed on Mar. 26, 2012.

(51) Int. Cl.
  *G01R 17/10* (2006.01)
  *G01N 27/327* (2006.01)

(52) U.S. Cl.
  CPC ........ *G01R 17/105* (2013.01); *G01N 27/3278* (2013.01)

(58) Field of Classification Search
  CPC ...... G01R 17/105; G01R 27/00–27/32; G01N 27/3278; G01N 27/04–27/205
  See application file for complete search history.

(56) References Cited

U.S. PATENT DOCUMENTS

| | | |
|---|---|---|
| 5,328,847 A | 7/1994 | Case et al. |
| 6,131,453 A | 10/2000 | Sultan et al. |
| 7,009,268 B2 | 3/2006 | Yang et al. |
| 2003/0079999 A1* | 5/2003 | Penner ............... B82Y 15/00 205/775 |
| 2004/0121509 A1 | 6/2004 | Meyer et al. |

OTHER PUBLICATIONS

Kumar et al., "Renovation of Gas Sensor Technology: A Review", *MASAUM Journal of Reviews and Surveys*, vol. 1, Issue 1, Sep. 2009, pp. 62-80.
Huang et al., "Silicone polymer chemical vapor sensors fabricated by direct polymer patterning on substrate technique (DPPOST)", *Sensors and Actuators B*, 116 (2006), pp. 2-10.

* cited by examiner

*Primary Examiner* — Gurpreet Kaur
(74) *Attorney, Agent, or Firm* — Richard M. Klein; Fay Sharpe LLP

(57) ABSTRACT

Sensor devices disclosed herein allow multiple analytes or organisms to be individually tagged and selectively detected. When a binding event occurs one or more nanoswitches close and the corresponding array resistance value produces a voltage imbalance in the Wheatstone Bridge. The voltage detected by the voltage meter will then exhibit unique value change corresponding to the particular nanoswitche(s) in the array that are closed due to a binding event. Similarly the same functionalization chemistry can be used on all nanoswitches so that the voltage detected by the voltage meter corresponds to concentration levels of the target analyte. Multiple functionalization chemistries on each switch can also be used to improve selectivity for more complex analytes. In some disclosed embodiments, the Wheatstone bridge voltage is tied to a predetermined resistance change rather than to smaller resistance changes that would occur from functionalization of one leg of a nanowire Wheatstone bridge.

19 Claims, 3 Drawing Sheets

CHEMICAL/BIOLOGICAL SENSORS EMPLOYING FUNCTIONALIZED NANOSWITCH ARRAY

This application claims the benefit of U.S. Provisional Application No. 61/615,519 filed Mar. 26, 2012 and titled "CHEMICAL/BIOLOGICAL SENSORS EMPLOYING FUNCTIONALIZED NANOSWITCH ARRAY". U.S. Provisional Application No. 61/615,519 filed Mar. 26, 2012 titled "CHEMICAL/BIOLOGICAL SENSORS EMPLOYING FUNCTIONALIZED NANOSWITCH ARRAY" is hereby incorporated by reference in its entirety into the specification of this application.

BACKGROUND

The following relates to the sensor arts, chemical sensing arts, biological organism sensing arts, and related arts.

Biological and chemical sensors find application in diverse areas, such as environmental monitoring, safety monitoring, potable water processing, and so forth. Highly sensitive sensor devices have been fabricated using on functionalized surfaces that interact with an analyte or organism of interest.

A chemical sensor employing functionalized nano-width regions as sensor elements is disclosed in Yang et al., U.S. Pat. No. 7,009,268. In this sensor, the resistances of a Wheatstone bridge are nano-width doped semiconductor regions (e.g., silicon, germanium, diamond, SiC, SiGe alloy, GaAs or another III-V semiconductor, GaN, or so forth) that are doped n-type or p-type. Metallic layers or lines are disposed at each of the four "corners" of the Wheatstone bridge to interconnect the nanowires. The nanowires include a sensing coating or other adaptation to produce a response to a stimulus such as a chemical or biological agent.

Meyers et al., U.S. Pub. No. 2004/0121509 A1 also discloses a nanowire-based Wheatstone bridge configured as a chemical sensor device. In this design, the four legs of the Wheatstone bridge include respective nanowires, one of which has a functionalized surface to act as a chemical sensor.

Such sensor devices can provide very high sensitivity, possibly even sufficient to detect a single analyte molecule, or a single biological cell of interest. However, the devices generate low power signals requiring substantial amplification, and can suffer from nonlinear response. Sensor devices employing power amplification may be unsuitable for use as wireless devices; however, wireless chemical sensors are advantageous in some applications in which the ambient is caustic or toxic, or the sensor device is intended to operate under high pressure, or in an otherwise challenging environment. The use of a high-precision bridge circuit such as a Wheatstone bridge can reduce or eliminate the need for amplification; however, the bridge circuit must be tuned with high precision (for example, by precisely matching resistances in a Wheatstone bridge) in order to realize the theoretically achievable high sensitivity.

BRIEF SUMMARY

In some embodiments disclosed herein, a sensor array comprises a plurality of sensing resistive electrical paths electrically arranged in parallel across sensor array electrical terminals. Each sensing resistive electrical path has a resistance value and a sensing switch that opens or closes the resistive electrical path responsive to the sensing switch detecting an analyte or organism of interest. The sensor array may further comprise a default resistive electrical path electrically arranged in parallel with the plurality of sensing resistive electrical paths across the sensor array electrical terminals, the default resistive electrical path having a default resistance value. In such embodiments, if all sensing switches are open then the sensor array has the default resistance value across the sensor array electrical terminals; whereas, if one or more sensing switches are closed then the sensor array has a resistance value across the sensor array electrical terminals equal to the parallel electrical combination of the default resistance value and the resistance value or values of the one or more sensing resistive electrical paths whose sensing switches are closed.

In some embodiments disclosed herein, a sensor device comprises: a sensor array comprising a plurality of sensing resistive electrical paths electrically arranged in parallel across sensor array electrical terminals, each sensing resistive electrical path having a resistance value and a sensing switch that opens or closes the resistive electrical path responsive to the sensing switch detecting an analyte or organism of interest; and a Wheatstone bridge having four legs wherein the sensor array is one of the four legs and is electrically connected into the Wheatstone bridge by the sensor array electrical terminals.

In some embodiments disclosed herein, a sensor device comprises: a sensor array comprising N sensing resistive electrical paths electrically arranged in parallel across sensor array electrical terminals, where N is an integer greater than or equal to two, each sensing resistive electrical path having a resistance value and a sensing switch that opens or closes the resistive electrical path responsive to the sensing switch detecting an analyte or organism of interest; and a resistance meter connected across the sensor array electrical terminals to measure the electrical resistance across the sensor array electrical terminals. In some embodiments the sensor array further comprises a default resistive electrical path electrically arranged in parallel with the N sensing resistive electrical paths across the sensor array electrical terminals, the default resistive electrical path having a default resistance value. In such embodiments, if all sensing switches are open then the sensor array has the default resistance value across the sensor array electrical terminals; whereas, if one or more sensing switches are closed then the sensor array has a resistance value across the sensor array electrical terminals equal to the parallel electrical combination of the default resistance value and the resistance value or values of the one or more sensing resistive electrical paths whose sensing switches are closed. In some embodiments the resistance meter comprises a Wheatstone bridge having four legs wherein the sensor array is one of the four legs and is electrically connected into the Wheatstone bridge by the sensor array electrical terminals. In some embodiments the sensor device further comprises a voltage source connected to apply a voltage to the Wheatstone bridge. In some such embodiments, the voltage source comprises a rectifying antenna converting microwave energy to generate the voltage applied to the Wheatstone bridge.

DETAILED DESCRIPTION OF PREFERRED EMBODIMENTS

Figure 1:
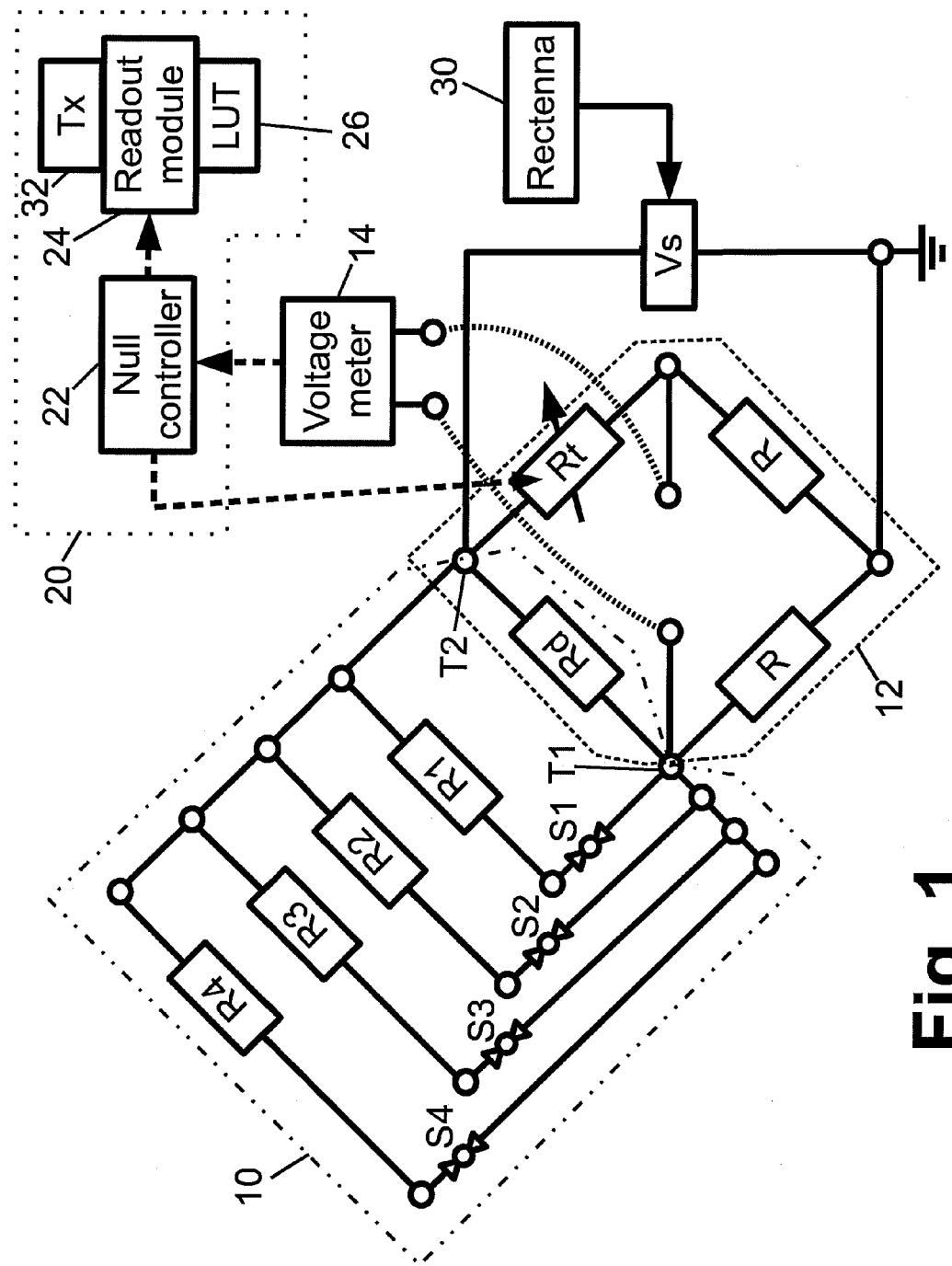
FIG. 1 diagrammatically shows an operative combination of a sensor array, Wheatstone bridge, voltage meter, and further processing circuitry.

With reference to FIG. 1, a sensor device includes a sensor array 10 comprising a plurality of sensing resistive electrical paths electrically arranged in parallel across sensor array electrical terminals T1, T2. The illustrative sensor array 10 includes four sensing resistive electrical paths; however, in general there may be N sensing resistive electrical paths where N is an integer greater than or equal to two. Each sensing resistive electrical path has a resistance value and a sensing switch S1, S2, S3, S4 that opens or closes the resistive electrical path responsive to the sensing switch detecting an analyte or organism of interest. In the illustrative example, the four sensing resistive electrical paths respectively have resistance values R1, R2, R3, and R4. In the illustrative example these resistance values R1, R2, R3, and R4 are indicated as lumped resistive elements (e.g., discrete resistor elements), which is typically a convenient configuration for manufacturing. However, the resistance value of a given sensing resistive electrical path may be constructed as a distributed resistance, or as an electrical series configuration or other electrical configuration of two or more distributed or lumped component resistances, or so forth.

Each of the illustrative four sensing resistive electrical paths includes a respective sensing switch S1, S2, S3, S4. If the resistance of a sensing switch (when closed) is not negligible, then its contribution to the total resistance of the sensing resistive electrical path is preferably incorporated into the resistance value. (For example, if the sensing switch S1 has a non-negligible resistance in the closed state, then the corresponding R1 should include this resistance. By way of quantitative example, if this path includes switch S1 with a closed state resistance of 50 ohms and the path further includes a lumped resistor having a resistor value of 750 ohms, then the total resistance R1 of the path is 800 ohms). Optionally, the sensing resistive electrical paths may include adjustable trim resistors (not shown) that enable fine-tuning of the resistance values R1, R2, R3, R4. The resistance values R1, R2, R3, R4 are accurately established, for example using low-tolerance discrete resistor elements trimmed with adjustable trim resistors to achieve a desired resistance value as measured by a precision electrical meter.

In the illustrative embodiment, the sensing switches S1, S2, S3, S4 are assumed to have a "normally open" configuration in which the sensing switch is normally in the open (i.e., electrically non-conducting) and only closes (that is, switches to an electrically conducting state) when the analyte or organism of interest is detected by the sensing switch. In some embodiments, subsequent removal of the analyte or organism of interest causes the sensing switch to re-open; in other embodiments, the switch remains closed even if the analyte or organism of interest is subsequently removed. In the former case the sensor array 10 is "dynamic" and senses the current presence or absence of the analyte or organism of interest (albeit possibly with some latency time); in the latter case the sensor array 10 provides a memory or storage (albeit possibly of limited total duration, and/or possibly resettable by suitable treatment of the sensor array 10 by heating, chemical washing, or some other regenerative processing).

Moreover, while in the illustrative example the switches S1, S2, S3, S4 are assumed to have a "normally open" configuration, the switches may alternatively have a "normally closed" configuration in which the switch is normally closed (i.e., electrically conducting) and only opens (i.e., becomes electrically non-conducting) when the analyte or organism of interest is detected by the switch.

The illustrative normally open sensing switches S1, S2, S3, S4 close when the analyte or organism of interest is detected by the switch. By "detected" or similar phraseology it is meant that the analyte or organism of interest comes into contact with a functionalized surface of the sensing switch, or otherwise operatively couples with the sensing switch, with the analyte or organism of interest at a concentration sufficient to trigger the sensing switch to close. In some embodiments, the sensing switches S1, S2, S3, S4 are nanoswitches with functionalized surfaces that trigger (e.g., close) upon detection of a single molecule of the analyte of interest, or that trigger upon detection of a single cell of the organism of interest. Alternatively, the one or more of the switches S1, S2, S3, S4 may be designed to trigger (e.g., close) when the analyte or organism of interest is detected at above a certain threshold concentration, or after a threshold number of molecules or cells contact the sensing surface of the sensing switch.

If the sensor array comprises only the plurality of sensing resistive electrical paths, then the resistance across the terminals T1, T2 is equal to the parallel combination of the resistance values of those sensing resistive electrical path or paths (if any) that have closed switches. This resistance will be infinite (i.e., an open circuit) if none of the switches S1, S2, S3, S4 is closed. The potential for such an "open-circuit" condition may be undesirable for some applications.

To avoid such an open-circuit condition, the illustrative sensor array 10 further includes a default resistive electrical path electrically arranged in parallel with the plurality of sensing resistive electrical paths across the sensor array electrical terminals T1, T2. The default resistive electrical path has a default resistance value Rd. The default resistive electrical path does not include a sensing switch, and is always electrically connected across the electrical terminals T1, T2. It follows that in the illustrative sensor array 10, the resistance seen across the terminals T1, T2 is equal to the default resistance value Rd in parallel with the resistance values (if any) of the sensing resistive electrical path or paths that have closed switches. Quantitatively, the resistance $R_{T1,T2}$ across the terminals T1, T2 is given by $$R_{T1,T2} = \left( \frac{1}{Rd} + \sum_{j \in J} \frac{1}{R_j} \right)^{-1}$$

where the set J denotes the set of all sensing resistive electrical paths having closed sensing switches. For the sensor array 10, $R_{T1,T2} \leq Rd$ holds, with $R_{T1,T2} = Rd$ holding when there are no closed sensing switches (i.e., the set J is empty). If one or more of the resistance values R1, R2, R3, R4 is also placed across the terminals T1, T2 by the corresponding switch S1, S2, S3, S4 being closed (so that the set J is no longer an empty set), then this resistance will be electrically in parallel with the default resistance Rd and accordingly will reduce the resistance $R_{T1,T2}$ across the terminals T1, T2. (Viewed another way, the switched-in closed path or paths partially shunt of the default resistance Rd, which lowers the total resistance $R_{T1,T2}$ seen at the terminals T1, T2).

The disclosed sensor arrays can be used in a variety of ways depending upon the functionalization chemistry and/or sensitivity levels of the constituent sensing switches S1, S2, S3, S4. In some embodiments the different switches S1, S2, S3, S4 are configured to detect different concentrations of the analyte or organism of interest. The sensor array 10 in such embodiments provides an automatically digitized value for the concentration of the analyte or organism of interest.

By way of illustrative quantitative example, consider an embodiment in which the illustrative four switches S1, S2, S3, S4 are configured to close upon detection of different concentrations of an analyte of interest as set forth in Table 1. The path resistance values R1, R2, R3, R4 and the default resistance value Rd are also given in Table 1 for this quantitative example. It is again emphasized that all resistances Rd, R1, R2, R3, and R4 are known a priori. Furthermore, these resistances are selected to be readily distinguishable from one another. For example, as shown in Table 1 each of the four resistances R1, R2, R3, and R4 has a different value, and moreover no combination of two (or three) resistance values equals any other resistance value.

TABLE 1

| Switch | Analyte threshold for closing | Path resistance |
|---|---|---|
| — | — | Rd = 1000 ohm |
| S1 | 2 g/cc | R1 = 800 ohm |
| S2 | 4 g/cc | R2 = 400 ohm |
| S3 | 6 g/cc | R3 = 200 ohm |
| S4 | 8 g/cc | R4 = 100 ohm |

For this quantitative example, Table 2 shows the resistance value $R_{T1,T2}$ at the sensor array electrical terminals T1, T2 for various concentrations of the analyte of interest.

TABLE 2

| Analyte concentration (C) | Active switch(es) | Resistance $R_{T1,T2}$ at terminals T1, T2 |
|---|---|---|
| C < 2 g/cc | None | 1000 ohm |
| 2 ≤ C < 4 g/cc | S1 | 444 ohm |
| 4 ≤ C < 6 g/cc | S1 and S2 | 210 ohm |
| 6 ≤ C < 8 g/cc | S1, S2, and S3 | 103 ohm |
| C > 8 g/cc | S1, S2, S3, and S4 | 51 ohm |

The resistance $R_{T1,T2}$ is "discretized" in that the resistance $R_{T1,T2}$ across the terminals T1, T2 assumes one of only five possible values (in this example), namely 1000 ohms, 444 ohms, 210 ohms, 103 ohms, or 51 ohms. These values are relatively widely spread out, i.e. the smallest difference from one level to the next is 52 ohms. As a result, even an electrical meter with coarse precision can ascertain the concentration "bin". Yet, the sensing switches S1, S2, S3, S4 may be of very high sensitivity. The use of the sensor array 10 effectively separates the sensitivity, which is controlled by the sensitivity of the switches S1, S2, S3, S4, from the electrical signal which is controlled by the resistance values R1, R2, R3, R4. Moreover, the discretized resistance levels for $R_{T1,T2}$ can be tuned by suitable selection of the constituent resistance values Rd, R1, R2, R3, R4, as well as by the number of sensing resistive electrical paths. If higher resolution is desired, then the number of sensing resistive electrical paths can be increased. If larger dynamic range is desired, then the sensitivities of the sensing switches can be redesigned.

In other applications, the sensor array 10 is configured to detect a complex composition of multiple analytes or organisms of interest. Toward this end, in some embodiments the different switches S1, S2, S3, S4 are configured to detect different analytes or organisms of interest. These applications rely upon different functionalization chemistries for the constituent sensing switches S1, S2, S3, S4. In these embodiments, different sensing switches are sensitive to different analytes or organisms of interest. By suitable selection of the corresponding resistance values Rd, R1, R2, R3, R4, the resistance $R_{T1,T2}$ at the terminals T1, T2 encodes which analyte or organism of interest, or which combination of analytes or organisms of interest, are present.

By way of illustrative quantitative example, consider an embodiment in which the illustrative four switches S1, S2, S3, S4 are configured to close upon detection of four different respective analytes of interest A, B, C, and D, as set forth in Table 3. For example, Table 3 shows that sensing switch S3 closes upon detection of the analyte C, whereas sensing switch S2 closes upon detection of the analyte B, and so forth. Resistance values R1, R2, R3, R4 of the respective sensing resistive electrical paths and the default resistance value Rd of the default resistance value Rd are also given in Table 3 for this quantitative example.

TABLE 3

| Switch | Analyte of interest | Path resistance |
|---|---|---|
| — | — | Rd = 600 ohm |
| S1 | A | R1 = 1000 ohm |
| S2 | B | R2 = 550 ohm |
| S3 | C | R3 = 300 ohm |
| S4 | D | R4 = 260 ohm |

Table 4 shows the resistance $R_{T1,T2}$ across the sensor array electrical terminals T1, T2 for various combinations of the analytes A, B, C, and D. There are $2^4$=16 possible combinations of the four analytes A, B, C, D. Any of these sixteen possible analyte combinations can be unambiguously identified based on the resistance $R_{T1,T2}$, as demonstrated by Table 4.

This result can be generalized as follows: for a sensor array with N sensing resistive electrical paths and suitable selection of the N resistance values for those paths, it is possible to encode up to $2^N$ possible outputs as different resistance levels across the sensor array electrical terminals T1, T2. In the example of Tables 3 and 4, all $2^N$=16 possible outputs are actually encode. However, in some embodiments not all of the $2^N$ potential combinations will be utilized. For example, the embodiment of Tables 1 and 2 uses only five combinations. This is a consequence of the lack of independence of operation of the four switches S1, S2, S3, S4 in that embodiment. For example, switch S1 is not independent of switch S2, because any time the switch S2 is closed it follows that the switch S1 must also be closed, since switch S1 closes at a lower analyte concentration threshold than switch S2 in the embodiment of Tables 1 and 2.

TABLE 4

| Closed switch(es) | Detected analyte(s) | Resistance $R_{T1,T2}$ across terminals T1, T2 |
|---|---|---|
| None | None | 600 ohm |
| S1 | A | 375 ohm |
| S2 | B | 287 ohm |
| S1 and S2 | A and B | 223 ohm |
| S3 | C | 200 ohm |
| S4 | D | 181 ohm |

TABLE 4-continued

| Closed switch(es) | Detected analyte(s) | Resistance $R_{T1,T2}$ across terminals T1, T2 |
|---|---|---|
| S1 and S3 | A and C | 167 ohm |
| S1 and S4 | A and D | 154 ohm |
| S2 and S3 | B and C | 147 ohm |
| S2 and S4 | B and D | 136 ohm |
| S1, S2, and S3 | A, B, and C | 128 ohm |
| S1, S2, and S4 | A, B, and D | 120 ohm |
| S3 and S4 | C and D | 113 ohm |
| S1, S3, and S4 | A, C, and D | 102 ohm |
| S2, S3, S4 | B, C, and D | 94 ohm |
| S1, S2, S3, and S4 | A, B, C, and D | 86 ohm |

Advantageously, the disclosed sensor arrays can be configured to provide strong signal differentiation controlled by the resistance values R1, R2, R3, R4 and default resistance value Rd. For example, considering the embodiment of Table 4, a measurement of the resistance across the terminals T1, T2 with uncertainty of as high as ±4 ohms is generally sufficient to distinguish all combinations of the analytes A, B, C, D, since even the closest two encoded $R_{T1,T2}$ values are separated by about 7 ohms.

With continuing reference to FIG. 1, the sensor device employs a Wheatstone bridge 12 to read out the sensor array 10. The Wheatstone bridge 12 includes four resistance legs, one of which is the sensor array 10 and another of which is a tunable resistor of tunable resistance Rt. The remaining two legs have the same resistance R. An applied voltage Vs is applied across the Wheatstone bridge and generates an output voltage that is measured by an illustrative voltage meter 14. It is readily seen that the output voltage is nulled (that is, set to zero) when the adjustable resistance value Rt is tuned to precisely equal the resistance $R_{T1,T2}$ across the sensor array electrical terminals T1, T2 (that is, the null condition is $R_{T1,T2}$=Rt).

In some embodiments, the tunable resistor leg is adjusted until the null condition is achieved, and the nulling resistance Rt=$R_{T1,T2}$ is read and used in conjunction with a suitable table such as Table 2 or Table 4 to generate a useful value (e.g., the measured analyte concentration range in the embodiment of Tables 1 and 2, or the combination of analytes A, B, C, and/or D in the embodiment of Tables 3 and 4).

With continuing reference to FIG. 1, in an alternative embodiment further processing circuitry 20 is provided to convert the null resistance to a useful value. In the illustrative example, a null controller 22 automatically adjusts the adjustable resistance value Rt until the voltage output by the voltage meter 14 is zero (in other words, the output of the voltage meter 14 provides feedback for the null controller 22 to adjust the resistance Rt to achieve the null condition). A readout module 24 receives the nulling Rt value and accesses a look-up table (LUT) 26 (for example, an electronic data structure equivalent to the first and third columns of Table 2, or an electronic data structure equivalent to the second and third columns of Table 4) to generate the useful result. The processing circuitry 20 is suitably embodied by a digital microprocessor or microcontroller and associated data memory for storing the LUT 26. For example, in some embodiments the processing circuitry 20 is a suitably programmed computer.

The sensor device of FIG. 1 can be variously configured. In some embodiments it is a wired sensor. In this case, electrical power input wires provide the supply voltage Vs to the Wheatstone bridge 12. In other embodiments the sensor device of FIG. 1 is configured as a wireless sensor device. In this embodiment, a rectifying antenna (or "rectenna") 30 (optionally along with suitable power conditioning circuit elements) suitably converts received microwave energy into the DC supply voltage Vs. In the wireless embodiment, the transmitter 32 suitably transmits the readout off the wireless sensor device. In variant embodiments, the transmitter may transmit an intermediate signal, such as the output of the null controller 22, with downstream processing components 24, 26 located off-sensor device and processing the signal transmitted by the sensor device.

Figure 2:
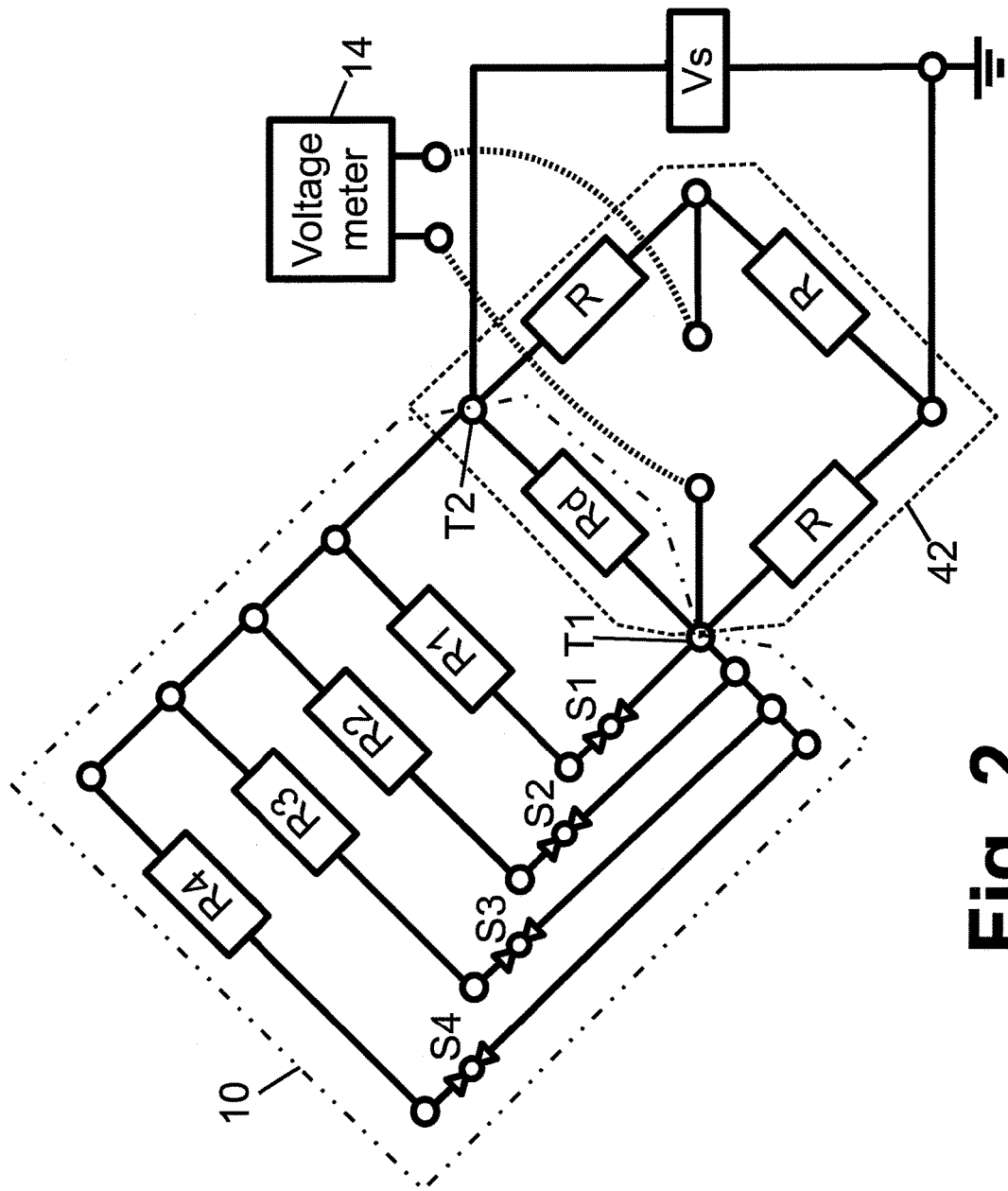
FIG. 2 diagrammatically shows a sensor device output configuration with a modified Wheatstone bridge as compared with the embodiment of FIG. 1.
Figure 3:
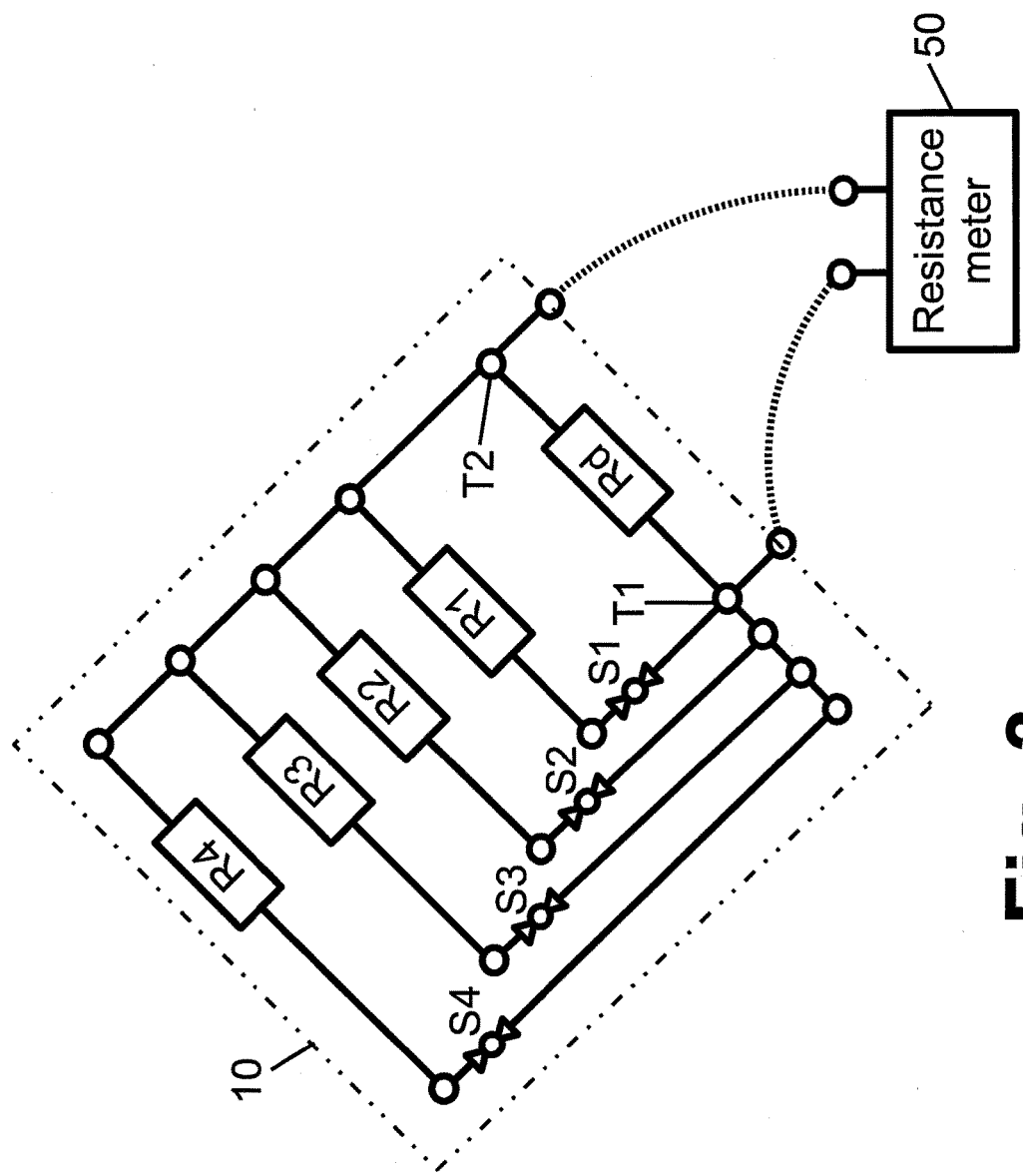
FIG. 3 diagrammatically shows a sensor device output configuration with a generalized resistance meter.

With reference to FIGS. 2 and 3, other sensor device output configurations are contemplated. In the embodiment of FIG. 2 a modified Wheatstone bridge 42 is identical with the Wheatstone bridge 12 of FIG. 1, except that the adjustable resistor leg having adjustable resistance value Rt is replaced by a fixed resistance leg having the same resistance value R as the two lower legs. Thus, the Wheatstone bridge 42 has the sensor array 10 as one leg, and the other three legs have fixed resistance value R. The voltage $V_{out}$ measured by the voltage meter 14 is $$V_{out} = V_S \cdot \left( \frac{R_{T1,T2} - R}{2(R_{T1,T2} + R)} \right).$$

If the supply voltage Vs and the resistances R are known values and $V_{out}$ is measured by the voltage meter 14, then $$R_{T1,T2} = R \cdot \left( \frac{V_S + 2V_{out}}{V_S - 2V_{out}} \right).$$

The precision with which this measurement can be performed is reduced as compared with the approach of balancing the bridge by adjusting Rt as in the embodiment of FIG. 1. However, the accuracy needed is not especially high, e.g. ±4 ohm in the case of the embodiment of Tables 3 and 4, or about ±20 ohm in the case of the embodiment of Tables 1 and 2. Moreover, if the default resistance value Rd of the sensor array 10 and the resistance values R of the other three legs of the Wheatstone bridge 42 are set equal, then $V_{out}$=0 if all switches S1, S2, S3, S4 are open such that $R_{T1,T2}$=Rd=R. This can be useful, for example, in that a detection event is signaled by $V_{out}$ deviating from the default zero value.

FIG. 3 illustrates a general sensor device in which the resistance $R_{T1,T2}$ across the sensor array electrical terminals T1, T2 is directly measured using a resistance meter 50, which can be any circuit configured to measure the resistance $R_{T1,T2}$, such as an analog or digital ohmmeter, or the illustrative Wheatstone bridge of FIG. 1 or FIG. 2, or so forth.

The disclosed sensor devices allow multiple analytes or organisms to be individually tagged and selectively detected based on closing of the unique functionalization chemistry/structure of each individual nanoswitch S1, S2, S3, S4. When a binding event occurs the nanoswitch closes and the corresponding array resistance value R1, R2, R3, or R4 produces a voltage imbalance in the Wheatstone Bridge 12, 42 (assuming in this embodiment that Rd=R so that the bridge 12, 42 is balanced when all switches S1, S2, S3, S4 are open). The voltage detected by the voltage meter 14 will then exhibit large unique value changes corresponding to the particular nanoswitch(es) in the array that are closed due to a binding event. Similarly the same functionalization chemistry can be used on all nanoswitches so that the voltage detected by the voltage meter 14 corresponds to concentration levels of the target analyte. Furthermore multiple functionalization chemistries on each switch can also be used to improve selectivity for more complex analytes for which a single selective functionalization layer does not exist. In the disclosed sensor devices, the Wheatstone bridge 12, 42 detection voltage is tied to a predetermined (and optionally large) resistance change rather being tied to the smaller resistance changes that would occur from the direct functionalization of one leg of a nanowire Wheatstone bridge. Another advantage of the disclosed sensor devices is that resistance of a functionalized nanowire does not have to be matched to the three other legs of a Wheatstone bridge.

Moreover, fabrication is simplified by only having to assemble the nanoswitches rather the entire Wheatstone bridge from the nanowire structure.

The preferred embodiments have been illustrated and described. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A sensor device comprising: a sensor array comprising a plurality of sensing resistive electrical paths electrically arranged in parallel across sensor array electrical terminals, each sensing resistive electrical path having a resistance value and a sensing switch that opens or closes the resistive electrical path responsive to the sensing switch detecting an analyte or organism of interest, wherein the sensing switch of each sensing resistive electrical path is normally closed and opens the sensing resistive electrical path responsive to the sensing switch detecting the analyte or organism of interest.

2. A sensor device, comprising:
a sensor array comprising:
a plurality of sensing resistive electrical paths electrically arranged in parallel across sensor array electrical terminals, each sensing resistive electrical path having a resistance value and a sensing switch that opens or closes the resistive electrical path responsive to the sensing switch detecting an analyte or organism of interest; and
a default resistive electrical path electrically arranged in parallel with the plurality of sensing resistive electrical paths across the sensor array electrical terminals, the default resistive electrical path having a default resistance value;
wherein if all sensing switches are open then the sensor array has the default resistance value across the sensor array electrical terminals; and
wherein if one or more sensing switches are closed then the sensor array has a resistance value across the sensor array electrical terminals equal to a parallel electrical combination of the default resistance value and the resistance value or values of the sensing resistive electrical path or paths whose sensing switch is closed.

3. The sensor device of claim 2, further comprising:
a Wheatstone bridge having four legs wherein the sensor array is one of the four legs and is electrically connected into the Wheatstone bridge by the sensor array electrical terminals.

4. The sensor device of claim 3, wherein the four legs of the Wheatstone bridge further include a nulling leg comprising an adjustable resistance that is adjusted to null a voltage output of the Wheatstone bridge, an output of the sensor being equal to or based upon the value of the adjustable resistance.

5. The sensor device of claim 4, wherein the four legs of the Wheatstone bridge are configured such that adjusting the adjustable resistance of the nulling leg to equal the resistance value across the sensor array electrical terminals nulls the voltage output of the Wheatstone bridge.

6. The sensor device of claim 2, wherein the sensor array includes N sensing resistive electrical paths, where N is an integer greater than or equal to two, with N different resistance values for the N different sensing resistive electrical paths selected such that the sensor array has a resistance value across the sensor array electrical terminals that encodes which if any of the N sensing resistive electrical paths is closed.

7. The sensor device of claim 6, wherein different sensing resistive electrical paths of the sensor array include sensing switches that detect different analytes or organisms of interest such that the sensor array has a resistance value across the sensor array electrical terminals that encodes which if any of the different analytes or organisms of interest are detected by the sensor device.

8. The sensor device of claim 7, wherein the sensor array has a resistance value across the sensor array electrical terminals that encodes one of $2^{N+1}$ levels representing one of the $2^N$ possible combinations of presence or absence of the different analytes or organisms of interest.

9. The sensor device of claim 6, wherein different sensing resistive electrical paths of the sensor array include sensing switches that detect different concentrations of the analyte or organism of interest such that the sensor array has a resistance value across the sensor array electrical terminals that encodes one of N+1 discrete concentration levels of the analyte or organism of interest.

10. The sensor device of claim 6, wherein the sensor array has a resistance value across the sensor array electrical terminals that encodes one of $2^{N+1}$ levels including a zero level representing one of the $2^N$ possible configurations of the sensor array.

11. A sensor device comprising:
a sensor array comprising a plurality of sensing resistive electrical paths electrically arranged in parallel across sensor array electrical terminals, each sensing resistive electrical path having a resistance value and a sensing switch that opens or closes the resistive electrical path responsive to the sensing switch detecting an analyte or organism of interest; and
a Wheatstone bridge having four legs wherein the sensor array is one of the four legs and is electrically connected into the Wheatstone bridge by the sensor array electrical terminals.

12. The sensor device of claim 11, wherein the four legs of the Wheatstone bridge further include a nulling leg comprising an adjustable resistance that is adjusted to null a voltage output of the Wheatstone bridge, an output of the sensor being equal to or based upon the value of the adjustable resistance.

13. The sensor device of claim 12, wherein the four legs of the Wheatstone bridge are configured such that adjusting the adjustable resistance of the nulling leg to equal the resistance value across the sensor array electrical terminals nulls the voltage output of the Wheatstone bridge.

14. A sensor device comprising:
a sensor array comprising N different sensing resistive electrical paths electrically arranged in parallel across sensor array electrical terminals, each sensing resistive electrical path having a resistance value and a sensing switch that opens or closes the resistive electrical path responsive to the sensing switch detecting an analyte or organism of interest, where N is an integer greater than or equal to two, with N different resistance values for the N different sensing resistive electrical paths selected such that the sensor array has a resistance value across the sensor array electrical terminals that encodes which if any of the N sensing resistive electrical paths is closed.

15. The sensor device of claim 14, further comprising:
a Wheatstone bridge having four legs wherein the sensor array is one of the four legs and is electrically connected into the Wheatstone bridge by the sensor array electrical terminals.

16. The sensor device of claim 15, wherein the four legs of the Wheatstone bridge further include a nulling leg comprising an adjustable resistance that is adjusted to null a voltage output of the Wheatstone bridge, an output of the sensor being equal to or based upon the value of the adjustable resistance.

17. The sensor device of claim 16, wherein the four legs of the Wheatstone bridge are configured such that adjusting the adjustable resistance of the nulling leg to equal the resistance value across the sensor array electrical terminals nulls the voltage output of the Wheatstone bridge.

18. The sensor device of claim 15, further comprising a voltage source connected to apply a voltage to the Wheatstone bridge.

19. The sensor device of claim 18, wherein the voltage source comprises a rectifying antenna converting microwave energy to generate the voltage applied to the Wheatstone bridge.

* * * * *